United States Patent [19]

Kunin

[11] Patent Number: 5,840,339
[45] Date of Patent: Nov. 24, 1998

[54] BLOOD CHOLESTEROL REDUCING PHARMACEUTICAL COMPOSITION

[76] Inventor: Robert Kunin, 860 Lower Ferry Rd.-Apt. 2J, Trenton, N.J. 08628

[21] Appl. No.: 939,990

[22] Filed: Sep. 3, 1992

Related U.S. Application Data

[63] Continuation-in-part of Ser. No. 737,705, Jul. 30, 1991, abandoned.

[51] Int. Cl.$^6$ .................................................. A61K 9/14
[52] U.S. Cl. .................... 424/489; 424/78.1; 424/483; 424/490; 424/497; 514/951
[58] Field of Search .................. 424/78.1, 483, 424/484, 489, 490, 497

[56] References Cited

U.S. PATENT DOCUMENTS 4,814,345  3/1989  Ghebre-Sellassie et al. ............ 424/440
5,071,646  12/1991  Malkowska et al. .................... 514/951

*Primary Examiner*—Thurman K. Page
*Assistant Examiner*—James M. Spear
*Attorney, Agent, or Firm*—Rockey, Milnamow & Katz, Ltd.

[57] ABSTRACT

A salt comprising the reaction product of nicotinic acid and an anion exchange resin having a degree of crosslinking with divinylbenzene of less than 4%. These salts are useful in reducing blood cholesterol levels.

6 Claims, 2 Drawing Sheets

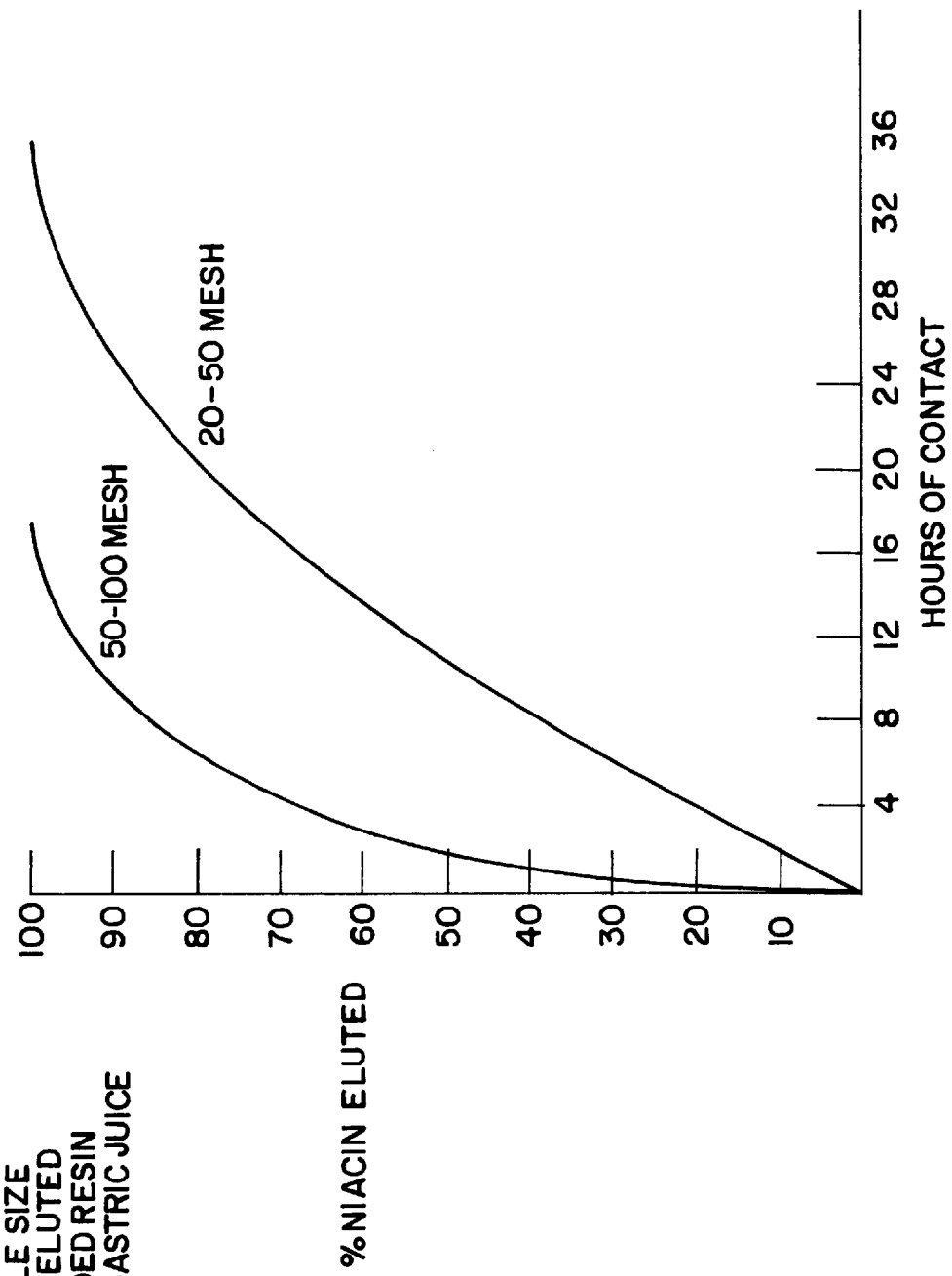

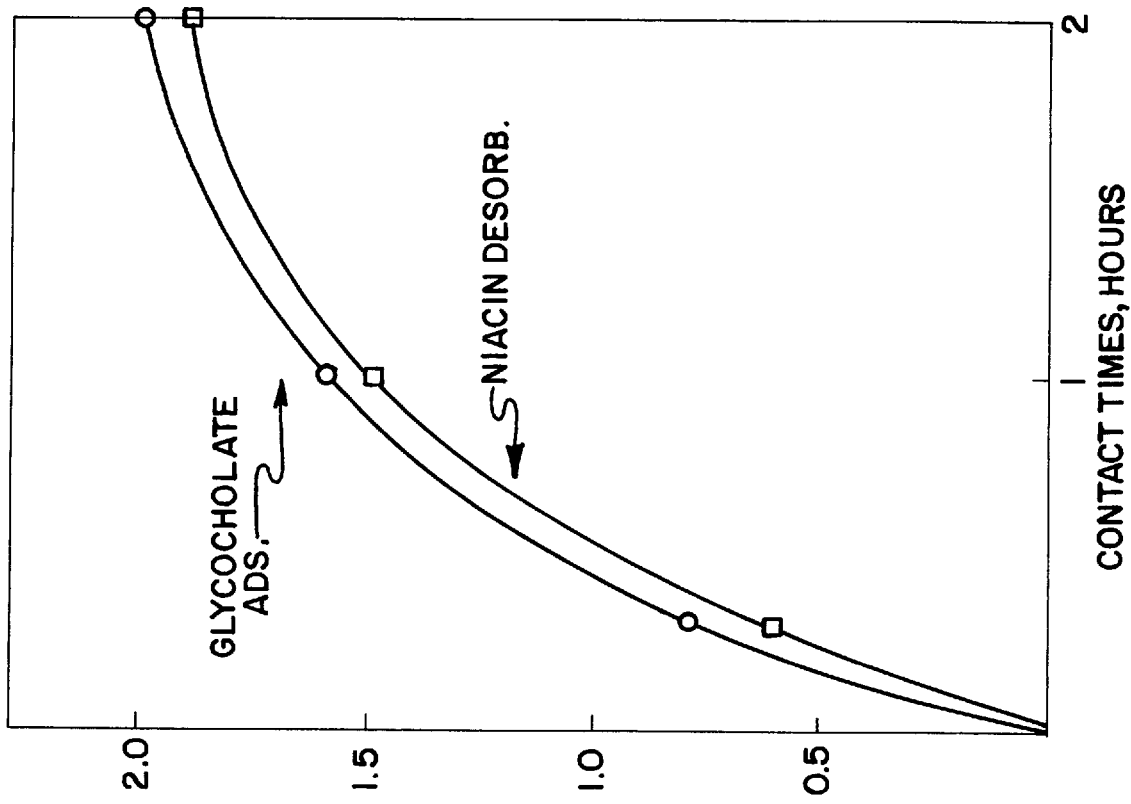

BLOOD CHOLESTEROL REDUCING PHARMACEUTICAL COMPOSITION

CROSS REFERENCE TO RELATED APPLICATIONS

This application is a continuation-in-part of U.S. application Ser. No. 07/737,705, filed Jul. 30, 1991 now abandoned.

FIELD OF THE INVENTION

The invention relates to an oral composition for reducing blood cholesterol levels.

BACKGROUND OF THE INVENTION

There are several oral compositions that have been proposed and, of these, some are currently being used for lowering blood cholesterol level. Some of the formulations or compositions are systemic and function in various ways after being absorbed into the blood stream. Others are non-systemic and function by binding the bile acids in the gastro-intestinal tract thereby reducing the amount of saturated fats absorbed into the blood stream. Examples of the former include niacin (nicotinic acid) and lovastatin [Vagelos, P. R., Science 252, 1080 (1991)]. Examples of the latter include various anion exchange resins commonly referred to as cholestyramine and colestipol. More recently, use of various combinations of some of the aforementioned compositions have been recommended. For example, the combined use of (1) cholestyramine and lovastatin, (2) essential fatty acids and cholestyramine, and (3) essential fatty acids and niacin have been proposed. (European Patent Application 0087864, 07-09-83, Inventor: D. F. Horrobin).

The use of ion exchange resins as a means for preparing sustained release pharmaceutical formulations has been described in U.S. Pat. Nos. 2,990,332 and 3,012,937. However, neither of these have involved the use of niacin nor have they been concerned with the control of blood cholesterol levels.

Other related references are included in the text, *Polym. Controlled Drug Delivery*, 1991, 215–230, CRC (Boca Raton, Fla.), Edited by J. Tarcha.

As with many medications, the aforementioned products and product combinations have serious side effects. For example, the cholestyramine or anion exchange resin therapy is usually administered in dosages sufficiently high so as to result in the removal of essential nutrients and vitamins and is accompanied by gastrointestinal upsets. Further, since it is administered in the chloride form excessive amounts of chlorides are released from the exchange of the chlorides with the bile acids, bicarbonates, sulfates and phosphates present in the gastro-intestinal juices. Although a vitamin, the high dosages of niacin (nicotinic acid) results in uncomfortable flushing in some patients. Further, niacin (nicotinic acid) may result in some side effects in some patients because of its moderate acidity.

SUMMARY OF THE INVENTION

The present invention relates to the combination of niacin and certain anion exchange resins, not as a mechanical mixture, but as a chemical salt, i.e., the salt of nicotinic acid and an anion exchange resin. More particularly, the present invention relates to a salt of nicotinic acid and an anion exchange resin with a degree of crosslinking with divinylbenzene of less than 4%.

The present invention also relates to a pharmaceutical composition containing the above mentioned salt and a pharmaceutically acceptable carrier and a method of reducing blood cholesterol levels comprising administering a therapeutically effective amount of the above mentioned salt to a patient in need of such treatment.

BRIEF DESCRIPTION OF THE DRAWINGS

FIG. 1 illustrates the effect of particle size on the rate of niacin eluted from niacin loaded ion exchange resin using simulated gastric juice; and FIG. 2 illustrates the dynamic adsorption of glycocholate and the simultaneous desorption of niacin using the niacin/resin salt of the present invention.

DETAILED DESCRIPTION OF THE INVENTION

As an example of the present invention, a salt of niacin and a quaternary ammonium anion exchange resin would have the following structure:

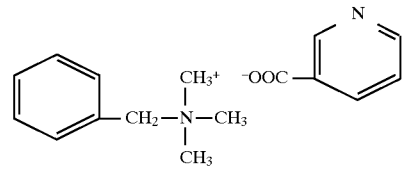

The salt of niacin and anion exchange resins can be formed by means of one of several ion exchange reactions such as the following:

1. reaction of the hydroxide or free base form of the anion exchange resin and nicotinic acid (niacin);
2. reaction of the bicarbonate forms of a strongly basic anion exchange resin and nicotinic acid;
3. reaction of the carbonate form of a strongly basic anion exchange resin and nicotinic acid; and
4. leaching of the chloride form of anion exchange resins with a solution of nicotinic acid.

The niacin/resin formulation serves the following basic functions:

1. control of the rate of niacin release; and
2. removal of some of the bile acid.

In essence, the formulation retains the cholesterol-lowering functions of niacin; however, the unique combination eliminates or decreases the following objectionable features of niacin:

1. flushing action of niacin;
2. acidity of niacin; and
3. removal of vitamins and nutrients.

The niacin release rate is controlled by varying the particle size and degree of crosslinking of the anion exchange resin. Increasing the particle size and degree of crosslinking of the anion exchange resin will decrease the rate in which the niacin will be released on contacting the juices in the gastro-intestinal tract. A multitude of niacin release-rate patterns are possible by combining variations of particle size and crosslinking. One may also control the rate of niacin release from the niacin salt of the anion exchange by coating the niacin-loaded resin with various polymer films such as those formed by various acrylic-based emulsions.

The choice of the anion exchange resin is quite critical; however, several choices are available. In essence, the basic strength of the anion exchange resin must be such that it can form a salt with nicotinic acid and the degree of crosslinking must be sufficiently low so as to permit the diffusion of the nicotinic acid into the gel structure of the anion exchange resin. All strongly basic anion exchange resins with degrees of crosslinking less than 4% divinylbenzene (DVB) are capable of forming salts with nicotinic acid.

Typical strongly basic anion exchange resins include those structures based upon crosslinked polystyrene, acrylates and vinylpyridine. Since the degree of crosslinking of such structures are difficult to determine on analysis of the ion exchange resin, a measure of the moisture content of the chloride form of the anion exchange resin when fully hydrated is frequently used as a measure of the effective degree of crosslinking. The moisture content varies inversely with the degree of crosslinking. A minimum moisture content of 50% (for the chloride form) has been found to correspond to the maximum degree of effective crosslinking for the purpose of this invention. This maximum limit has been found to apply for the selection of both strongly as well as weakly basic anion exchange resins.

The selection of weakly basic anion exchange resins for the purpose of this invention requires a knowledge of the basic strength of the weakly basic anion exchange resin. The basic strength of the strongly basic anion exchange resin is immaterial for the purpose of this invention since all of the strongly basic anion exchange resins are sufficiently basic to form salts with niacin or nicotinic acids. However, such is not the case for the weakly basic anion exchange resins. For example, weakly basic anion exchange resins prepared by the crosslinking of vinylpyridine and divinylbenzene are so weakly basic that they cannot form a salt with weak acids such as nicotinic acid. The basic strengths of weakly basic anion exchange resins can be measured by the technique employed by Gustafson, et al., [I & E. C. Fund, December 7 (68)] which determines the pKb of the anion exchange resin from the acid/base titration curve. By means of this measurement, it has been found that weakly basic anion exchange resins, for the purpose of this invention must have a pKb less than pKb 8.5.

The choice of the anion exchange resin determines its niacin capacity and hence the quantity of resin required for a particular niacin dosage. Further, the choice of the anion exchange resin also determines the quantity of bile acids removed per unit of niacin released. If one assumes the average capacity of the anion exchange resin to be 4 milliequivalents per gram (dry, chloride form), Table 1 describes the resin dosage required for various daily niacin requirements. These dosage levels are based upon the equivalent weight of niacin (nicotinic acid) to be 123.11 and assumes the anion exchange resin to be fully loaded with nicotinic acid.

TABLE 1

RESIN DOSAGE LEVELS FOR
VARIOUS DAILY NIACIN REQUIREMENTS

| NIACIN REQUIREMENTS (Grams) | RESIN DOSAGES (Grams) |
|---|---|
| 0.25 | 0.51 |
| 0.50 | 1.02 |
| 1.00 | 2.04 |
| 1.50 | 3.06 |
| 2.00 | 4.08 |

Representative suitable commercially available anion exchange resins include Amberlite IRA-268, a strongly basic anion exchange resin, available from Rohm and Haas Company, Philadelphia, Pa., Dowex SBR-P, a similar product available from Dow Chemical Company, Midland, Mich., and Dowex MWA-1, a weakly basic anion exchange resin also available from Dow Chemical Company.

An unexpected aspect of the nicotinic acid/anion exchange resin interactions is the release of the nicotinic acid. Normally, cyclical or aromatic organic acids are held by the anion exchange resins, particularly those containing aromatic structure with such tenacity that the adsorption is essentially (Gustafson et al.) [I & E. C. Prod. Res. & Dev., 7, 116 (68)] irreversible. Hence, one would not expect the niacin to be released readily on contact with the gastro-intestinal fluids. Were it not for this unexpected reversibility for the exchange of the absorbed nicotinic acid with the ionic composition of the gastro-intestinal ionic compositions, the niacin/anion exchange resin formulation would be worthless.

The pharmaceutical compositions of the present invention include one or more of the compounds of this invention formulated into compositions together with one or more non-toxic physiologically acceptable carriers, adjuvants or vehicles which are collectively referred to herein as carriers, for parenteral injection, for oral administration or solid or liquid form, for rectal or topical administration, and the like.

The compositions can be administered to humans and animals either orally, rectally, parenterally (intravenously, intramuscularly or subcutaneously) intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspension or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate of dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any needed preservatives, buffers or propellants as may be required. Ophthalmic formulations, eye ointments, powders and solutions are also contemplated as being within the scope of this invention.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the IL-1β pro inhibiting compounds of the present invention, stabilizers, preservatives, excipients, and the like. The preferred lipids are the phospholipids and the phosphatidyl cholines (lecithins), both natural and synthetic.

Methods for forming liposomes are known in the art. See, for example, *Methods in Cell Bioloy*, Ed. by Prescott, Volume XIV, Academic Press, New York, N.Y. p.33 et seq., (1976).

Actual dosage levels of active ingredient in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the inhibitor compounds of this invention administered to a host in single or divided doses may be in amounts, for example, of from about 0.1 mg to about 160.0 mg per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The invention will be more completely illustrated by the following representative examples:

EXAMPLE 1

25 ml. of Amberlite IRA-268 were placed in a 50 ml. buret and backwashed with water. The resin had a particle size of 20–50 mesh. The 25 ml. of resin had an anion exchange capacity of 20.0 milliequivalents. 250 ml. of a 0.1 normal solution of nicotinic acid were passed through the resin column at a flow rate of 0.13 ml/ml resin/min. The column was then rinsed with 100 ml. of deionized water and the two effluents (nicotinic acid and rinse water effluents) combined and titrated for acidity. By subtracting the milliequivalents of acid in the effluents from the quantity of nicotinic acid in the feed to the column, it was possible to calculate the quantity of nicotinic acid absorbed by the resin. This value corresponded to a loading equivalent to 99.5% of the theoretical capacity of the anion exchange resin.

EXAMPLE 2

The niacin-loaded column of Example 1 was eluted with 275 ml. of synthetic gastric juice at a flow rate of 0.13 ml/ml resin/min. and rinsed with deionized water. The eluate and rinse were combined and analyzed for niacin. 98.5% of the absorbed niacin was eluted.

EXAMPLE 3

The niacin-loaded resin of Example 1 was placed in a stirred reactor and agitated with the simulated gastric juice of Example 2 and the juice analyzed periodically for a period of 24 hours. The data obtained from this experiment are described in FIG. 1.

EXAMPLE 4

The experiments of Example 1 and 3 were repeated using a 50–100 mesh particle size. The data obtained from this experiment are also described in FIG. 1.

The experiments contained in Example 1–4 illustrate the reversibility of the absorption process involving nicotinic acid and anion exchange resins and the effect of particle size of the kinetics of the exchange process.

To test the potential efficiency of the niacin/cholestyramine salt as a lipid regulating agent, one must demonstrate that, when dispersed in the simulated juices and the stomach and upper intestine, the niacin should be eluted from the resin and the cholestyramine should be able to adsorb the glycocholate (bile acid). It is important to demonstrate that the niacin should be eluted from the cholestyramine and thereby be free for its absorption into the bloodstream. As the niacin is desorbed, the resin becomes free to absorb the glycocholate. The glycocholate may also desorb the niacin rendering it free to be absorbed by the bloodstream. The niacin is a systemic drug and the cholestyramine is a non-systemic drug. The niacin must be absorbed into the bloodstream to be effective whereas the cholestyramine cannot and need not be adsorbed to be effective. The latter functions by adsorbing the glycocholate (bile acid) and thereby preventing the bile acids from "carrying" fats into the bloodstream where the cholesterol is formed.

Tables 1 and 2 of U.S. Pat. No. 4,814,354 and the specification of said patent clearly state that the lipid lowering agent is strongly bound to the cholestyramine resin thereby seriously limiting the effectiveness of both components of the salt at the pH levels of the upper intestine—the area where the "action" takes place.

With the aforementioned discussion in mind, several experiments were performed which are summarized in Examples 5 and 6.

EXAMPLE 5

A sample of the niacin of the cholestyramine (Amberlite XE-268, Rohm and Haas Co.) was prepared according to the procedure described in Example 1. The niacin loading was 0.54 g./g of resin. The niacin/resin salt was contacted with stirring for 1 hr. at 37° C. with a simulated gastric juice pH 1.2) described in Table A at a resin/liquid ration of 1/170. After the first contact, the liquid phase was analyzed for niacin and the resin was filtered and re-contacted with fresh gastric juice for another 1 hour period. The liquid phase was analyzed for niacin as before. The data obtained are summarized in Table B.

TABLE A

COMPOSITION OF BIOLOGICAL FLUIDS
Meg./liter

| Ion | Gastric Juice | Small Intestine | Large Intestine |
| --- | --- | --- | --- |
| Potassium | 10 | 4–5 | 8.6 |
| Sodium | 50 | 140 | 151 |
| Calcium | 2.0–4.3 | 2.5–6.4 | 5.0 |
| Magnesium | 1.8–7.8 | 1–2 | 1.6 |

TABLE A-continued

COMPOSITION OF BIOLOGICAL FLUIDS
Meg./liter

| Ion | Gastric Juice | Small Intestine | Large Intestine |
| --- | --- | --- | --- |
| Chloride | 141 | 74–103 | 87.5 |
| Sulfate | — | — | — |
| Phosphate | 0.34–1.3 | 2.6107.66 | 17 |
| Bicarbonate | 0–21 | 2–32 | 91.8 |
| pH | 1.2–1.8 | 6.16–7.31 | 8.03 |
| Acidity/Alk. | 123.3 | 158.2 | 164.6 |

TABLE B

BATCH TREATMENT OF NIACIN/RESIN SALT
WITH SIMULATED GASTRIC JUICE

| Contact | % Niacin Eluted |
| --- | --- |
| First | 82% |
| Second | 16% |

EXAMPLE 6

This experiment was conducted in two parts and both involved the substitution of a synthetic upper intestinal juice (see Table A) containing sodium glycocholate in place of the gastric juice employed in the previous experiment (A). The intestinal juice had a pH of 6.5 and the concentration of the sodium glycocholate was 5 mg/ml. Two samples, 200 ml. each, were contacted with 1 g. of cholestyramine. One sample of resin contained no niacin and the other was the niacin/cholestyramine salt as described in Experiment A. The reaction vessels were stirred for 2 hours at 37° C. The resins were filtered and the fluid analyzed for glycocholate and for niacin and glycocholate in the case of the niacin/resin salt. The data are described in Table C.

TABLE C

BATCH TREATMENT OF CHOLESTYRAMINE AND
THE NIACIN/CHOLESTYRAMINE SALT WITH
SIMULATED UPPER INTESTINAL JUICE
CONTAINING SODIUM GLYCOCHOLATE

| | Case A Cholestyramine | Case B Niacin/Resin Salt |
| --- | --- | --- |
| Mg. Glycocholate ads./g. resin | 1010 | 950 |
| Mg. Niacin Desorbed/g. resin | — | 234 |
| Meq. Glycocholate ads./g. resin | 2.0 | 1.9 |
| Meq. Niacin Desorbed/g. resin | — | 1.9 |

FIG. 2 contains a plot of the data obtained during the course of Experiment B. The data illustrate the unusual adsorption of glycocholate and simultaneous desorption of niacin.

What is claimed is:

1. A salt comprising the reaction product of nicotinic acid and a basic anion exchange resin having a degree of crosslinking with divinylbenzene of less than about 4%, a maximum degree of crosslinking corresponding to a minimum moisture content of 50%, and a particle size in water in a swollen, chloride form ranging from about 0.03 to about 0.84 mm.

2. A method of reducing blood cholesterol levels comprising administering a therapeutically effective amount of a compound of claim 1 to a patient in need of such treatment.

3. A salt according to claim 1 in which the anion exchange resin is a weakly basic anion exchange resin having a pKb less than about 8.5.

4. A salt according to claim 1 in which the particles are enterically coated with a water soluble polymer film.

5. A salt according to claim 1 in which the composition is a powder having a particle size distribution in the 0.01 mm to 0.10 mm range.

6. A pharmaceutical composition comprising a salt of claim 1 and a pharmaceutically acceptable carrier.

* * * * *